United States Patent
Zeng et al.

(10) Patent No.: US 9,895,220 B2
(45) Date of Patent: Feb. 20, 2018

(54) MITRAL BILEAFLET VALVE

(71) Applicant: Horizon Scientific Corp., Irvine, CA (US)

(72) Inventors: Min Frank Zeng, Irvine, CA (US); Pham Lo, Irvine, CA (US)

(73) Assignee: Venus Medtech (Hangzhou) Inc. (CN)

( * ) Notice: Subject to any disclaimer, the term of this patent is extended or adjusted under 35 U.S.C. 154(b) by 0 days.

(21) Appl. No.: 15/426,935

(22) Filed: Feb. 7, 2017

(65) Prior Publication Data
US 2017/0143486 A1 May 25, 2017

Related U.S. Application Data

(63) Continuation of application No. 14/595,433, filed on Jan. 13, 2015, now Pat. No. 9,579,195.

(51) Int. Cl.
*A61F 2/24* (2006.01)

(52) U.S. Cl.
CPC .......... *A61F 2/2412* (2013.01); *A61F 2/2418* (2013.01); *A61F 2/2436* (2013.01); *A61F 2220/0075* (2013.01); *A61F 2230/0006* (2013.01); *A61F 2230/0008* (2013.01); *A61F 2230/0034* (2013.01)

(58) Field of Classification Search
CPC .............................. A61F 2/2412; A61F 2/2418
See application file for complete search history.

(56) References Cited

U.S. PATENT DOCUMENTS

| | | | |
|---|---|---|---|
| 3,739,402 A | 6/1973 | Cooley et al. | |
| 4,605,407 A | 8/1986 | Black et al. | |
| 2004/0122513 A1 | 6/2004 | Navia et al. | |
| 2005/0149181 A1 | 7/2005 | Eberhardt | |
| 2005/0228496 A1 | 10/2005 | Mensah et al. | |
| 2010/0280606 A1* | 11/2010 | Naor ...................... | A61F 2/2418 623/2.18 |
| 2013/0013058 A1 | 1/2013 | Umezu et al. | |
| 2013/0310928 A1* | 11/2013 | Morriss ................. | A61F 2/2418 623/2.12 |

OTHER PUBLICATIONS

PCT Search Report and Written Opinion for PCT/US2015/68020 dated Jun. 3, 2016.

* cited by examiner

*Primary Examiner* — Christopher D Prone
*Assistant Examiner* — Suba Ganesan
(74) *Attorney, Agent, or Firm* — Raymond Sun (57) ABSTRACT

A heart valve assembly has a leaflet support structure and a leaflet assembly. The leaflet support structure has a wire frame that supports the leaflet assembly. The leaflet assembly has first and second separate leaflets, each of which is comprised of a skirt section and a sinus leaflet section. Each skirt section has a flange portion and a body portion that has a smaller diameter than the flange portion, with the body portion having opposing side edges, and a curved opening defined by a first stitching edge at about the central portion of the body portion. Each sinus leaflet section has an outflow edge, and a curved second stitching edge, with the sinus leaflet section stitched to the skirt section along the first and second stitching edges. The opposing side edges of the body portion of the first leaflet are stitched to the corresponding side edges of the body portion of the second leaflet.

6 Claims, 15 Drawing Sheets

MITRAL BILEAFLET VALVE

BACKGROUND OF THE INVENTION

1. Field of the Invention

The present invention is directed to methods, systems, and apparatus for safely replacing or repairing native heart valves with prosthetic heart valves.

2. Description of the Prior Art

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, but such surgeries are dangerous and prone to complication.

More recently a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Unlike the aortic valve, however, the mitral valve annulus does not provide a good landmark for positioning a replacement mitral valve. In patients needing a replacement aortic valve, the height and width of the aortic annulus are generally increased in the presence of degenerative disease associated with calcium formation. These changes in tissue make it easier to properly secure a replacement aortic valve in place due to the reduced cross-sectional area of the aortic annulus. The degenerative changes typically found in aortic valves are not, however, present in mitral valves experiencing regurgitation, and a mitral valve annulus is therefore generally thinner than the annulus of a diseased aortic valve. The thinner mitral valve annulus makes it relatively more difficult to properly seat a replacement mitral valve in the native mitral valve annulus. The general anatomy of the mitral valve annulus also makes it more difficult to properly anchor a replacement mitral valve in place. The mitral valve annulus provides for a smoother transition from the left atrium to the left ventricle than the transition that the aortic valve annulus provides from the aorta to the left ventricle. The aortic annulus is anatomically more pronounced, providing a larger "bump" to which a replacement aortic valve can more easily be secured in place.

Thus, the larger mitral valve annulus makes it difficult to securely implant current percutaneously delivered valves in the native mitral position. Some attempts have been made to deliver and implant a one-piece replacement mitral valve, but it is difficult to provide a device that can be collapsed down to have a sufficiently small delivery profile and still be able to be expanded and secured in place within the mitral valve via a vascular access site.

As a result, there remains a need for a replacement mitral valve that has a valve support structure or anchoring device that can be positioned near or within the native mitral valve.

SUMMARY OF THE DISCLOSURE

To accomplish the objectives set forth above, the present invention provides a heart valve assembly that has a leaflet support structure and a leaflet assembly.

The leaflet support structure has a wire frame having an anterior atrium annulus section and a posterior atrium annulus section, with each opposite end of the atrium annulus sections transitioning to a commissure section that curves radially inwardly along the same plane as the atrium annulus sections. Each commissure section transitions via a first bend to a leg which extends vertically at opposite central points of the wire frame. Each leg extends vertically and slightly radially outwardly at an angle, and each leg transitions via a second bend which extends radially outwardly and transitions into a tail that extends vertically upwardly, with a gap defined between each corresponding tail and leg.

The leaflet assembly has first and second separate leaflets, each of which is comprised of a skirt section and a sinus leaflet section. Each skirt section has a flange portion and a body portion that has a smaller diameter than the flange portion, with the body portion having opposing side edges, and a curved opening defined by a first stitching edge at about the central portion of the body portion. Each sinus leaflet section has an outflow edge, and a curved second stitching edge, with the sinus leaflet section stitched to the skirt section along the first and second stitching edges. The opposing side edges of the body portion of the first leaflet are stitched to the corresponding side edges of the body portion of the second leaflet.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
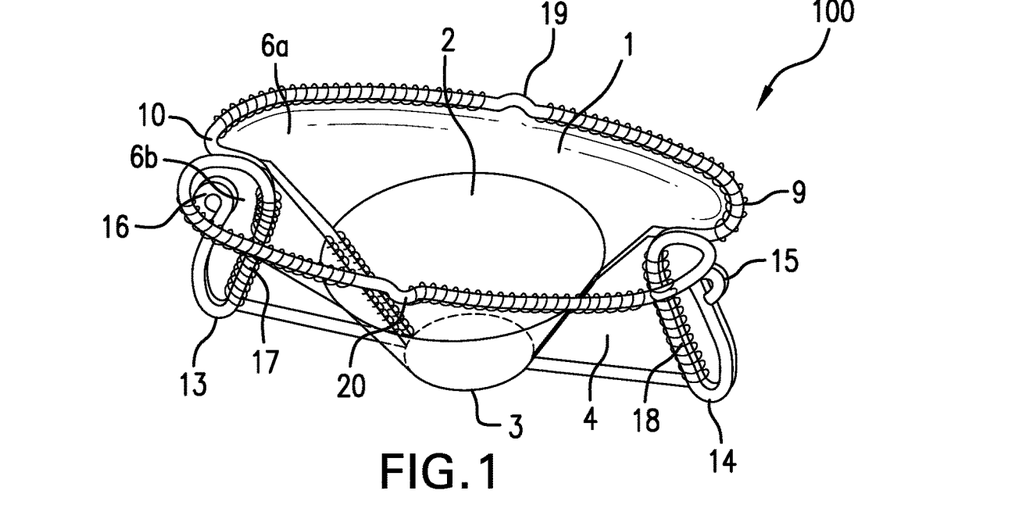
FIG. 1 is a perspective view of a mitral valve device according to one embodiment of the present invention.

The present invention provides a mitral valve device 100 that is shown in fully assembled form in FIG. 1. The device 100 has a wire frame 102 (see FIGS. 2A-2C) that is adapted to carry an integrated leaflet assembly 104 (see FIGS. 3A-4D). The wire frame 102 provides a simple leaflet valve support structure that can be effectively secured at the native mitral valve annulus. In addition, the leaflet assembly 104 provides a novel leaflet configuration which provides fast opening and closing of the valve leaflets. The overall construction of the device 100 is simple, and effective in promoting proper mitral valve function.

Figure 1A:
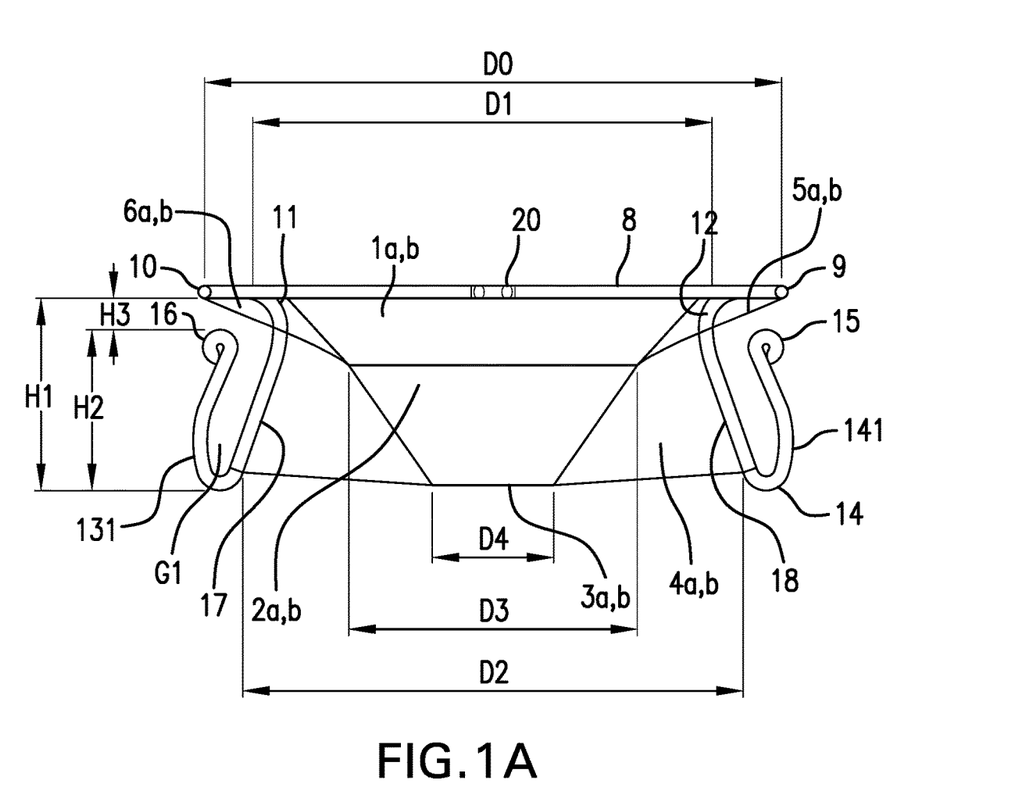
FIG. 1A is a schematic side view of the device of FIG. 1 shown with dimensions according to one non-limiting embodiment thereof, shown with the valve in a naturally open position without any pressure on the leaflets.
Figure 1B:
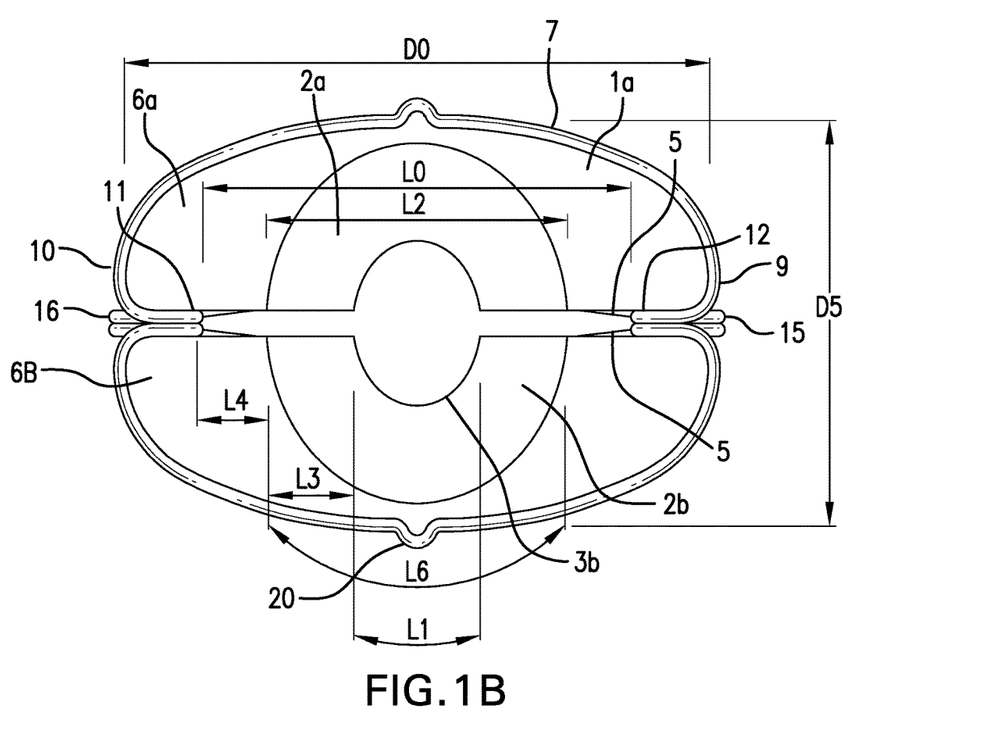
FIG. 1B is a schematic top view of the device of FIG. 1A shown with dimensions according to one non-limiting embodiment thereof, shown with the valve in a naturally open position without any pressure on the leaflets.
Figure 1C:
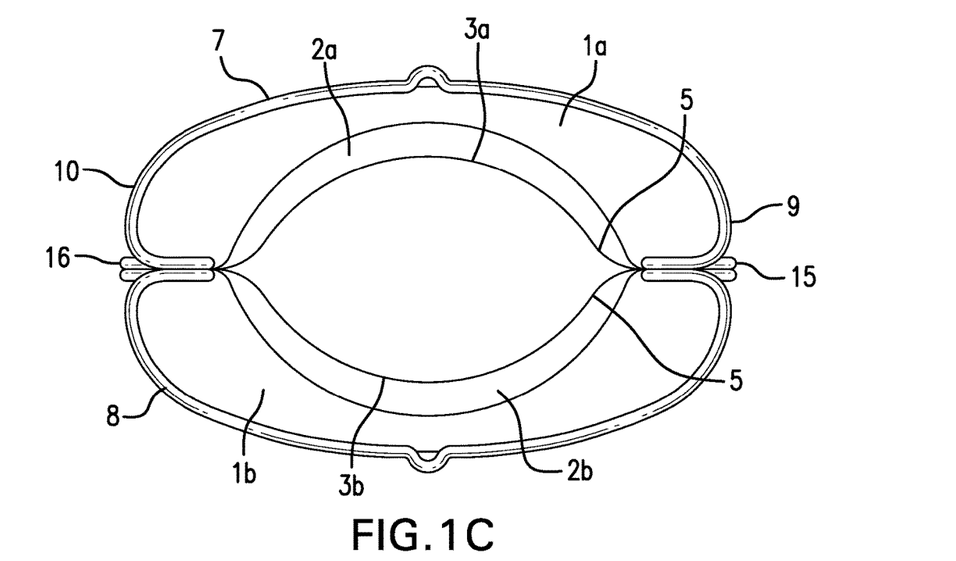
FIG. 1C is a top view of the device of FIG. 1 shown with the valve in a fully opened position with pressure on the leaflets.
Figure 1D:
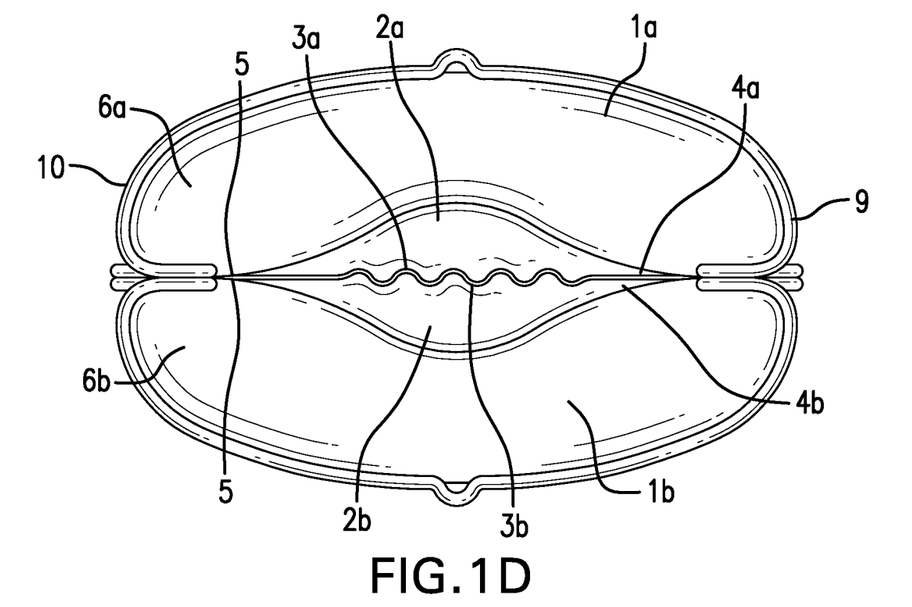
FIG. 1D is a top view of the device of FIG. 1 shown with the valve in a fully closed position with pressure on the leaflets.
Figure 1E:
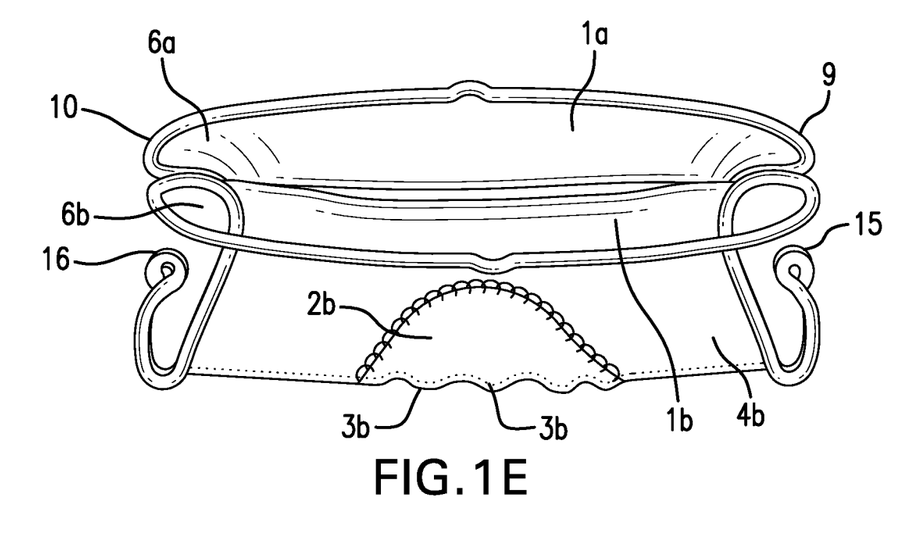
FIG. 1E is a side view of the device of FIG. 1 shown with the valve in a fully closed position with pressure on the leaflets.
Figure 2A:
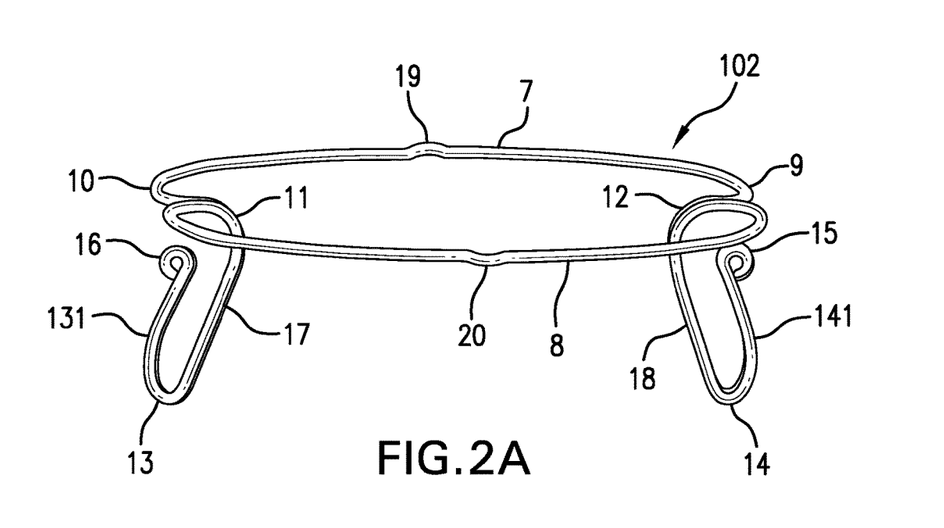
FIG. 2A is a perspective view of the wire frame of the mitral valve device of FIG. 1.
Figure 2B:
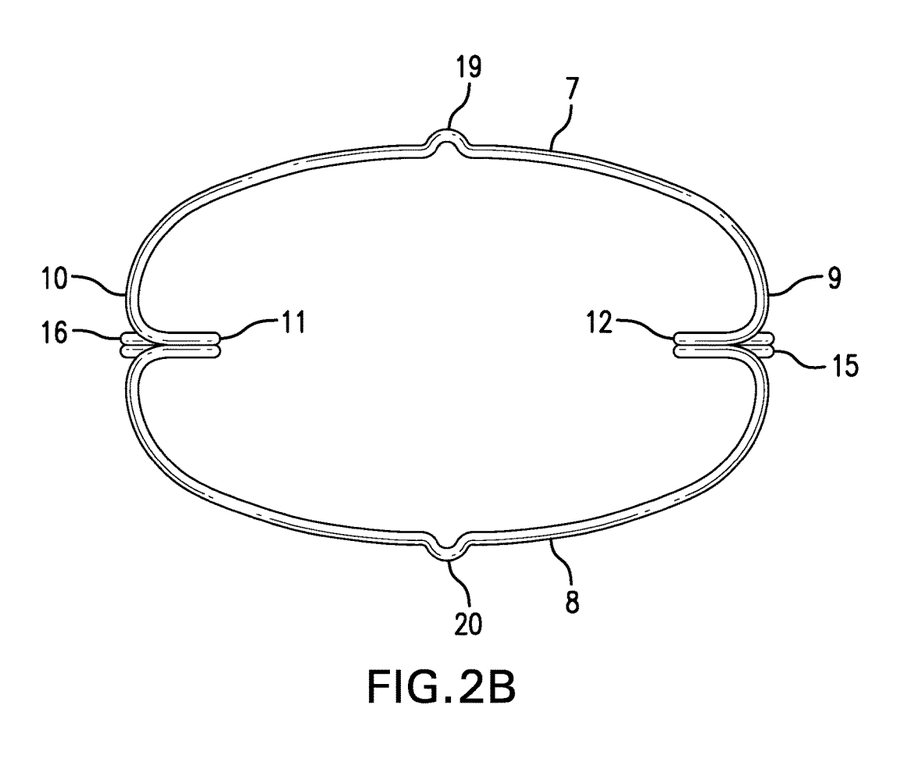
FIG. 2B is a top view of the wire frame of FIG. 2A.
Figure 2C:
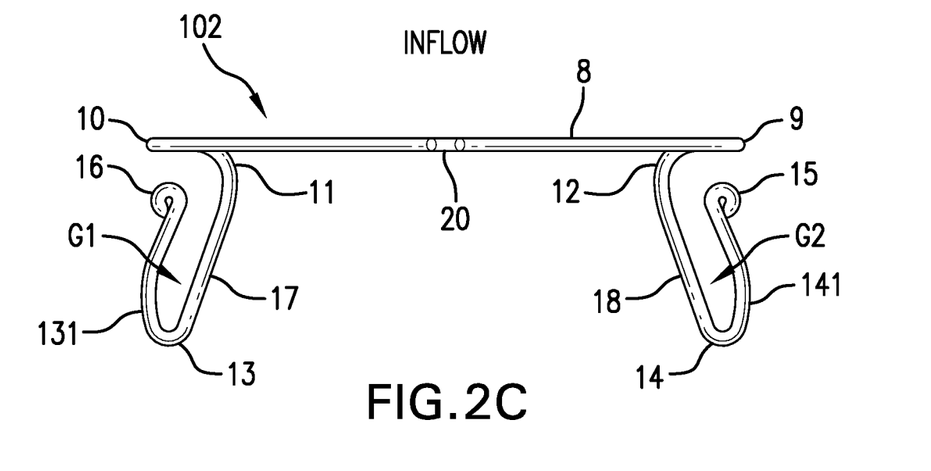
FIG. 2C is a side view of the wire frame of FIG. 2A.
Figure 3A:
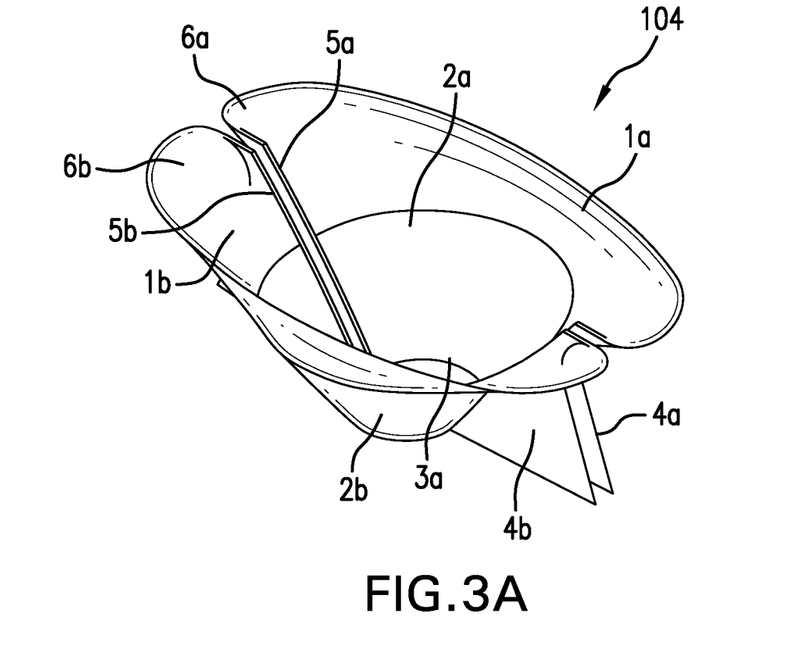
FIG. 3A is a perspective conceptual view of the leaflet assembly of the mitral valve design of the device of FIG. 1.
Figure 3B:
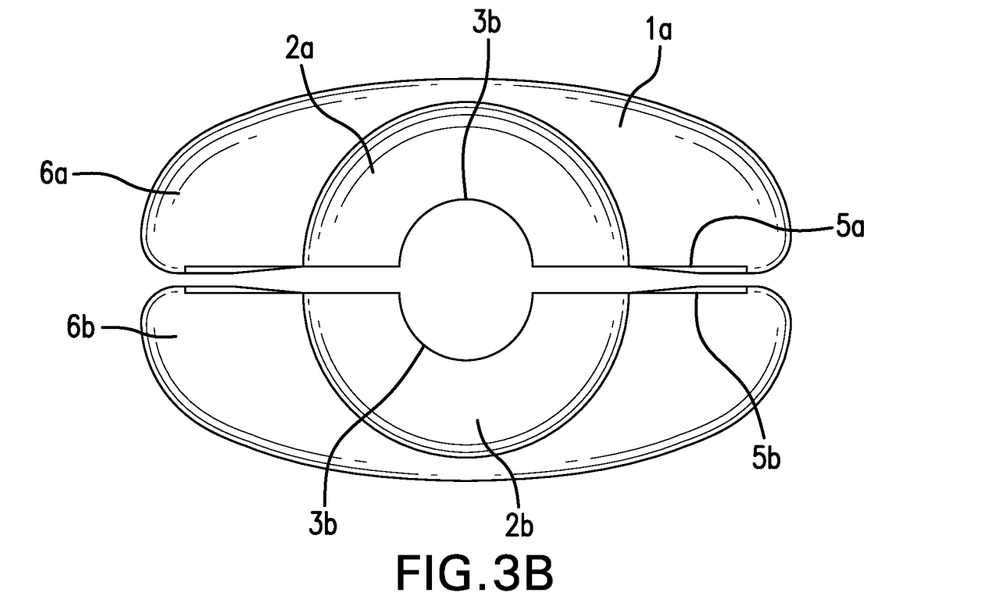
FIG. 3B is a top conceptual view of the leaflet assembly design of FIG. 3A.
Figure 3C:
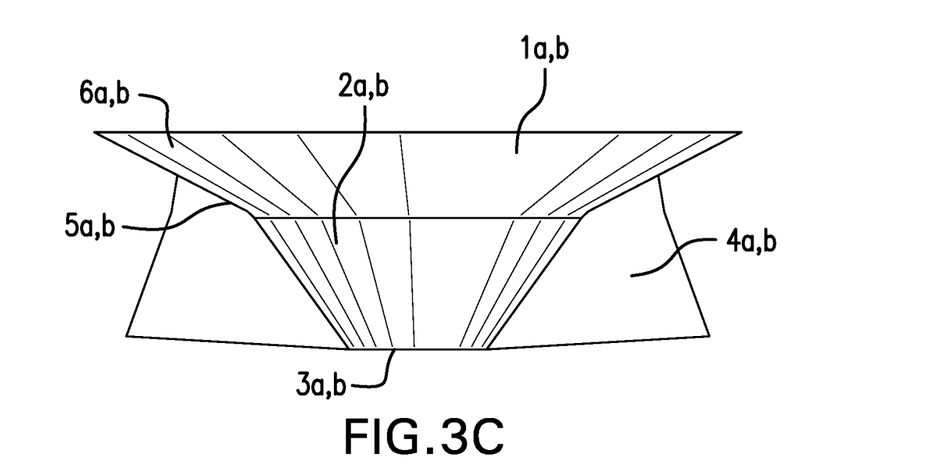
FIG. 3C is a side conceptual view of the leaflet assembly design of FIG. 3A.
Figure 3D:
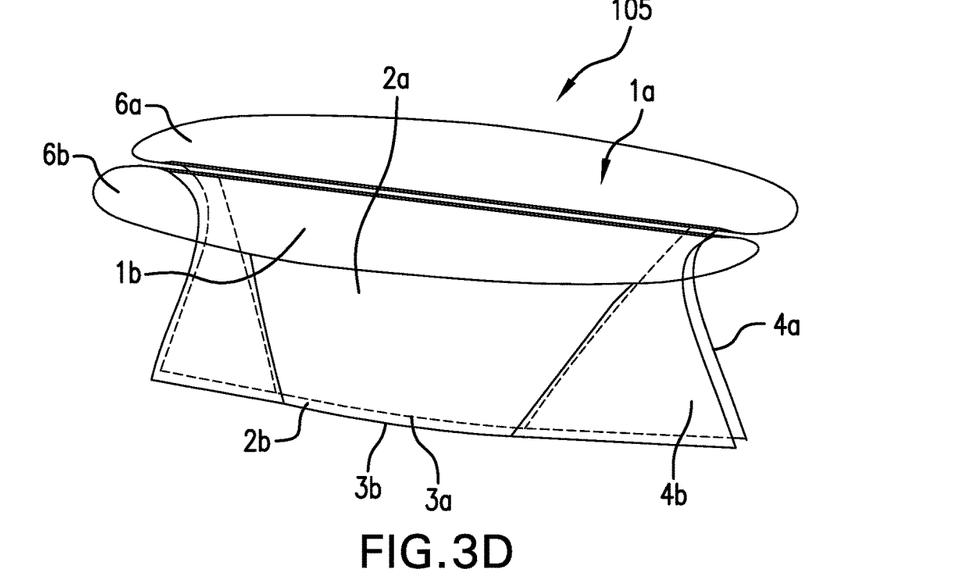
FIG. 3D is a conceptual view of the leaflet assembly design of FIG. 3A.
Figure 8:
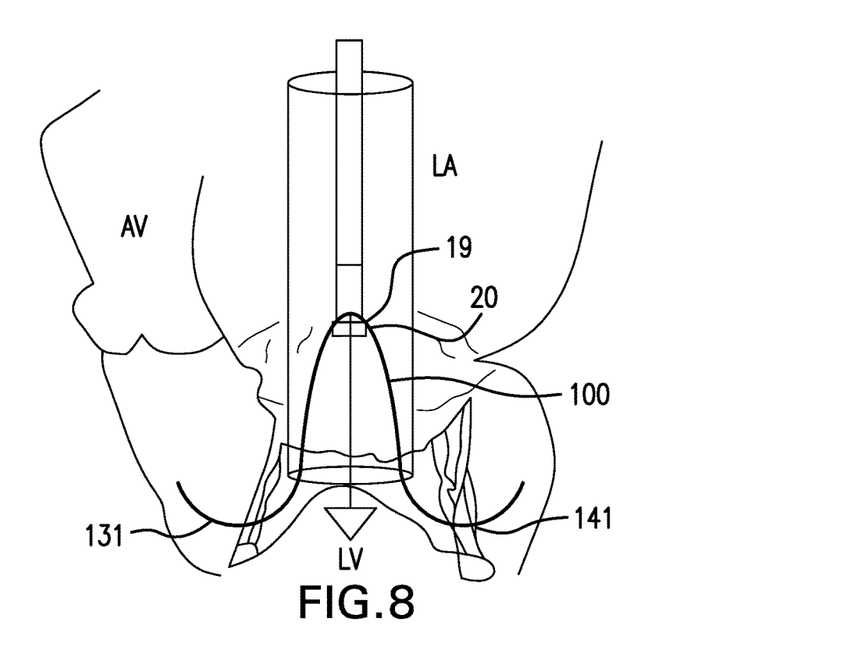
FIG. 8 illustrates how the device of FIG. 1 can be deployed at the mitral annulus of a patient's heart using a (transfemoral or transseptal) percutaneous delivery system.

As shown in FIGS. 1-2C, the wire frame 102 comprises an anterior atrium annulus section 7 and a posterior atrium annulus section 8, each of which extends horizontally and is shaped like half an oval. A U-shaped extension 19 and 20 is provided at about the central portion of each section 7 and 8, respectively, and extends radially outwardly. These extensions 19 and 20 function to seat the device 100 on the native annulus, and for use in being held by the hooks 191 and 201 of the delivery system (see FIG. 8) during percutaneous delivery. Each opposite end of the atrium annulus sections 7 and 8 transitions to a commissure section 9 and 10 that curves radially inwardly along the same plane as the atrium annulus sections 7 and 8, and then transitions via bends 11 and 12 to legs 17 and 18 which extend vertically at opposite central points of the wire frame 102. Each leg 17 and 18 extends vertically and slightly radially outwardly at an angle (see FIG. 2C), and transitions via bends 13 and 14, respectively, which extend radially outwardly and transition into tails 131 and 141, respectively, that extend vertically upwardly before terminating at rounded ends 16 and 15, respectively, which curve radially outwardly. Gaps G1 and G2 are defined between the tail 131 and the leg 17, and the tail 141 and 18, respectively. The wire frame 102 can define an oval shape (when viewed from the top), a circular shape, or a D shape.

FIGS. 1A and 1B illustrate some exemplary dimensions for the device 100 as follows:

D0: 38 mm
D1: 29 mm
D2: 34 mm
D3: 19 mm
D4: 8 mm
D5: 24 mm
H1: 13 mm
H2: 10 mm
H3: 2 mm
L0: 28 mm
L1: 13 mm
L2: 19 mm
L3: 6 mm
L4: 5 mm
L5: 29 mm
L6: 30 mm

These exemplary dimensions can be used for a device 100 that is adapted for use at the native mitral valve location for a generic adult and these dimensions will vary for devices 100 that are used for other applications, such as for a triscupid valve. These exemplary dimensions illustrate the proportions of the various elements to each other.

The wire frame 102 can be made of one continuous wire, and can be made from a thin wall biocompatible metallic element (such as stainless steel, Co—Cr based alloy, Nitinol™, Ta, and Ti etc.). As an example, the wire can be made from a Nitinol™ wire that is well-known in the art, and have a diameter of 0.2" to 0.4".

Referring to FIGS. 3A through 4D, the present invention provides a novel leaflet assembly 104 that provides a better coaptation between the leaflets. The leaflet assembly 104 provides two separate leaflets, each of which is comprised of an upper skirt section 1a or 1b, and a lower sinus leaflet section 2a or 2b. In other words, sections a and 2a make up one leaflet, and sections 1b and 2b make up the other leaflet. As best shown in FIGS. 4A-4D, the skirt sections 1a and 1b are identical, and each has a larger-diameter semi-oval flange portion 6a or 6b, and a smaller-diameter body portion 4a or 4b. Each body portion 4a or 4b has opposing side edges 26a that function as commissure folding lines along which the side edges 26a may be stitched to assemble the two separate leaflets into a single leaflet assembly 104. Each body portion 4a or 4b also has a central U-shaped opening defined by stitching edge 29, which is adapted to receive the curved edge of the corresponding sinus leaflet section 2a or 2b. Each skirt section 1a, 1b creates an oval-shaped site on the top of the natural annulus.

Each sinus leaflet section 2a or 2b has a generally semi-circular shape, including an outflow edge 3a or 3b, and a curved edge defined by stitching edge 31. Each sinus leaflet section 2a or 2b is stitched along its stitching edge 31 to the stitching edge 29 of the corresponding body portion 4a or 4b.

Figure 4A:
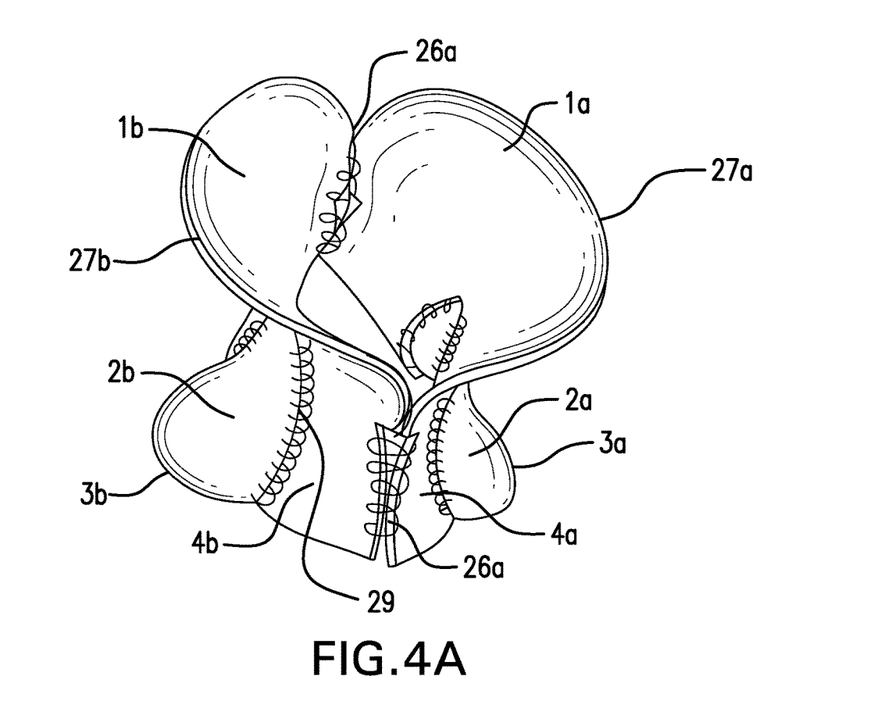
FIG. 4A is a perspective view of one embodiment of the leaflet assembly with the tissue of the mitral valve device of FIG. 1 that is based on the conceptual model shown in FIGS. 3A-3D.
Figure 4B:
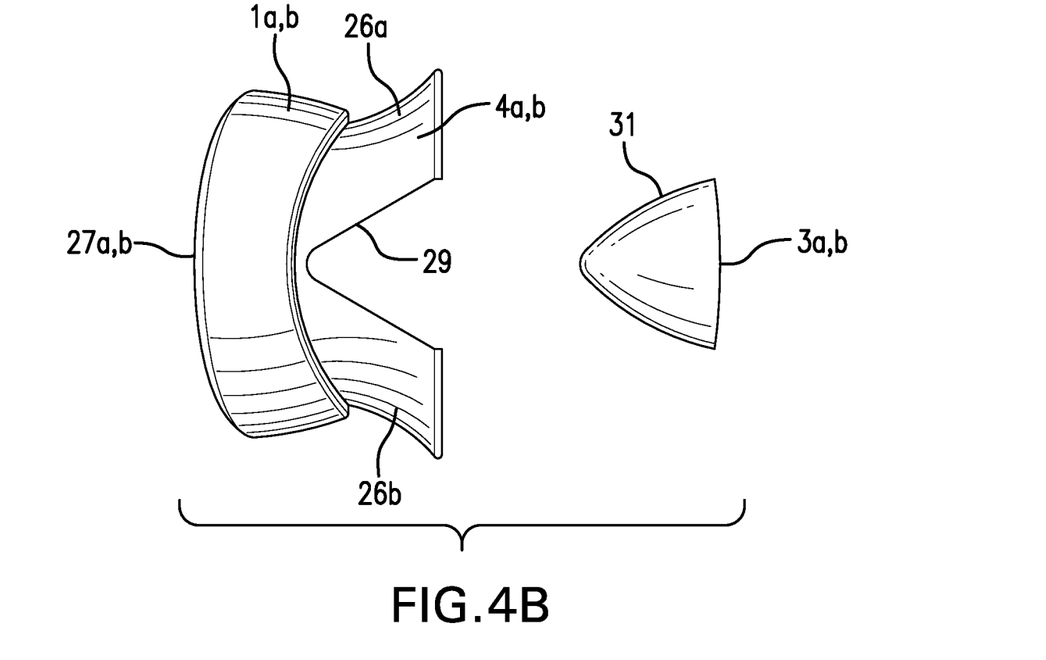
FIG. 4B is an exploded side view of one of the leaflets of the leaflet assembly of FIG. 4A.
Figure 4C:
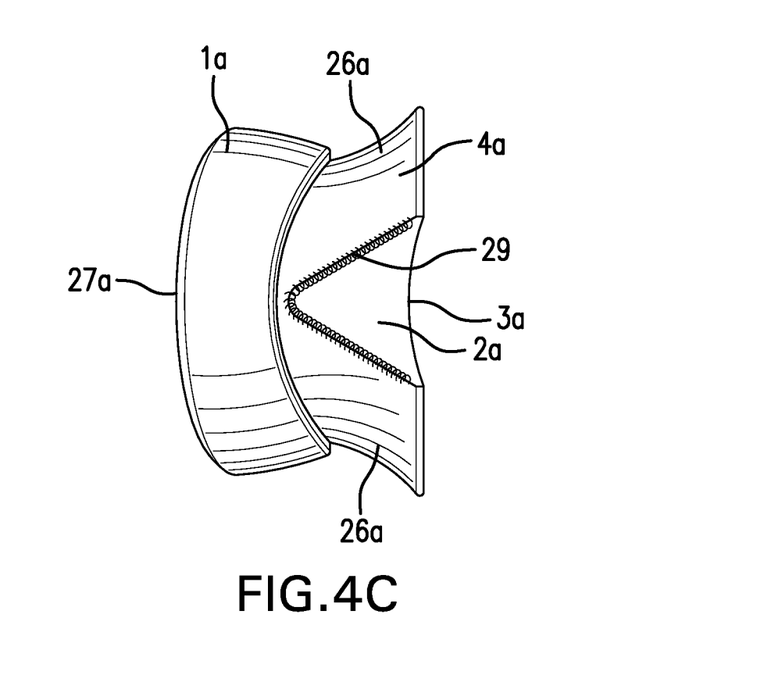
FIG. 4C is a side view of the leaflet assembly of FIG. 4A.
Figure 4D:
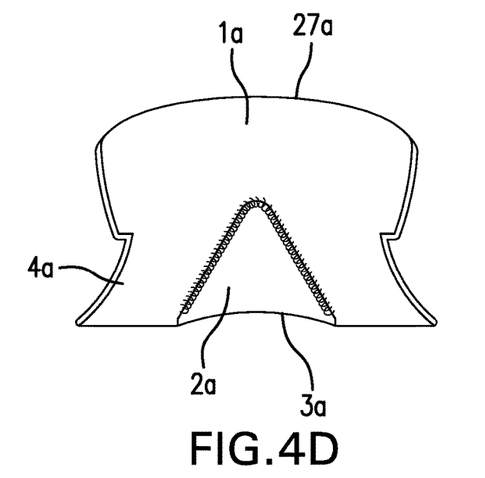
FIG. 4D is an inside view of one of the leaflets of the leaflet assembly of FIG. 4A.
Figure 4E:
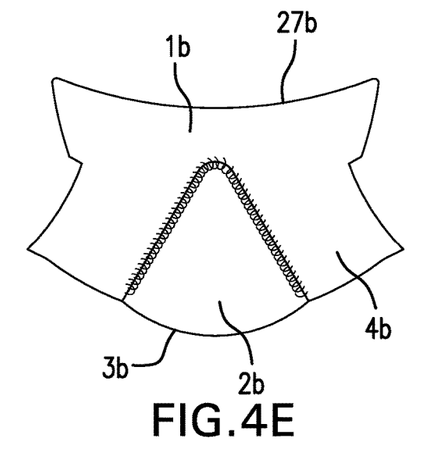
FIG. 4E is an outside view of one of the leaflets of the leaflet assembly of FIG. 4A.

The construction of the leaflet assembly 104 provides six components that correspond to the natural six components found in a native mitral valve. For example, FIG. 6D is a top view of a natural mitral valve with six natural components labeled by A1, A2, A3 and P1, P2, P3. Referring now to FIG. 4A, the leaflet assembly 104 has the same six components where 4a, 2a and 4a correspond to A1, A2 and A3, respectively, and 4b, 2b, 4b correspond to P1, P2 and P3, respectively. For this reason, the leaflet assembly 104 is able to function in a manner which comes closest to replicating the natural function of the native mitral valve.

Figure 5A:
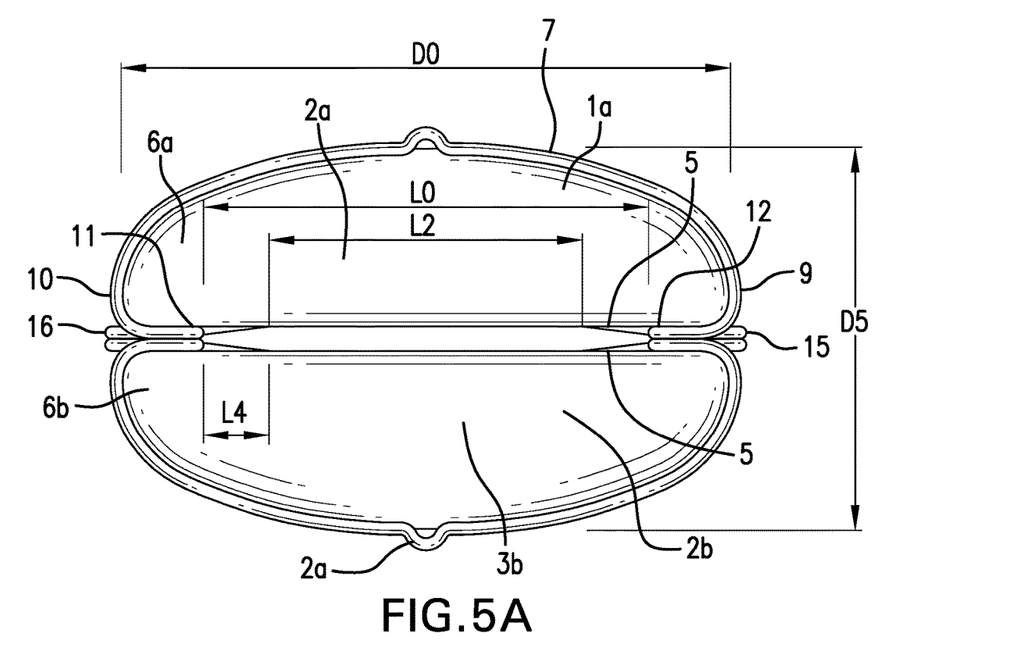
FIG. 5A is a top view illustrating the closing of a conventional bileaflet valve assembly using the wire frame of FIG. 2A.
Figure 5B:
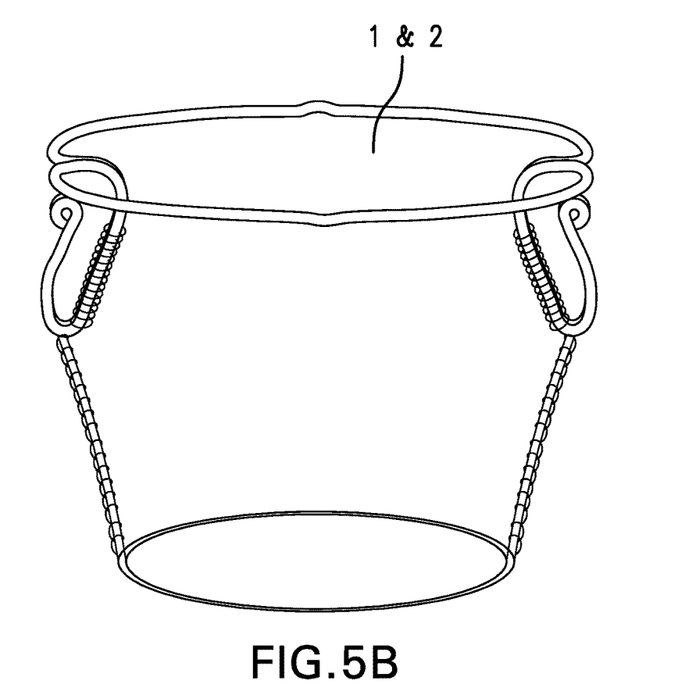
FIG. 5B is a perspective view illustrating the closing of a conventional bileaflet valve assembly.

In addition, with the leaflet construction shown in FIGS. 3A-4D, the leaflet assembly 104 of the present invention provides for a shorter valve assembly which facilitates improved coaptation. For example, FIG. 5A illustrates the wire frame 102 used with a conventional bi-leaflet valve assembly where the two leaflets must necessarily be long enough so as to allow for proper coaptation at the outflow end. In contrast, by sewing the body portions 4a, 4b together in a flat or folded manner as shown in the conceptual drawings of FIGS. 3A-3C, the sinus leaflet sections 2a, 2b can function to provide better leaflet coaptation along its outflow edges 3a, 3b while maintaining a shorter or lower profile. This in turn allows the skirt sections 1a, 1b to have a shorter profile. A shorter profile can be important because, if the valve body is too long, it could potentially interfere with the blood flow in the aortic direction.

To illustrate the benefits provided by the novel leaflet assembly shown in FIGS. 3A-4D, compare the dimensions in FIG. 1B using the novel leaflet design of the present invention with the dimensions in FIG. 5A for a conventional bi-leaflet valve assembly. In FIG. 1B, the valve design provides a "belly sinus" for a large opening. Using the dimensions in FIG. 1B, when the valve opens, the opening has a width of 35 mm, which is obtained by adding L1 (13 mm)+2×L4 (5 mm)+2×L3 (6 mm)=35 mm. In contrast, the opening provided by a conventional bi-leaflet valve in FIG. 5A would be L0, which is 28 mm.

The novel leaflet design of the present invention allows the valve to open and close faster because a valve with a shorter profile and having the sinus 2a, 2b will allow for the valve to open and close completely. The leaflet coaptation length will be short when the valve closes, and with the control provided by the body portions 4a, 4b when the valve is closed, this would allow the valve to open more quickly. In contrast, in a conventional bileaflet design, the leaflet coaptation length will be longer for the valve when it is fully closed, which takes too much time and requires greater pressure for the valve to open. Given the fact that a natural mitral valve usually opens at a pressure of 15 mm Hg and closes at a pressure of 140 mm Hg, these features of the novel leaflet design of the present invention allows for faster opening and closing of the valve.

Referring also to FIGS. 1, 2A-2C and 4A-4E, the side edges 26a illustrate stitch lines along which the body portions 4a, 4b may be stitched to the legs 17 and 18 of the wire frame 102. In addition, the edges 27a and 27b are attached to the annulus sections 7 and 8 of the wire frame 102. The skirt sections 1a and 1b sit on the commissures of the native leaflets along the lines 5.

The leaflet sections 1a, 1b, 2a and 2b can all be made from treated animal tissue such as pericardium, or from biocompatible polymer material (such as PTFE, Dacron, bovine, porcine, etc.). The leaflet sections 1a, 1b, 2a, 2b can also be provided with a drug or bioagent coating to improve performance, prevent thrombus formation, and promote endotheliolization, and can also be treated (or be provided) with a surface layer/coating to prevent calcification.

Figure 6A:
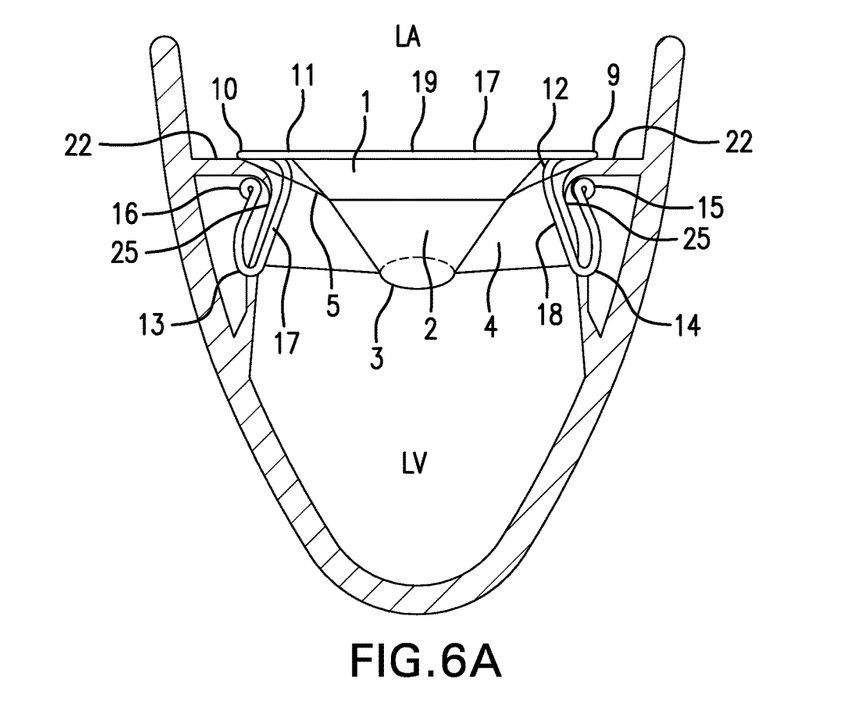
FIG. 6A is a side view of a patient's heart showing the deployment of the device of FIG. 1 at the mitral annulus position.
Figure 6B:
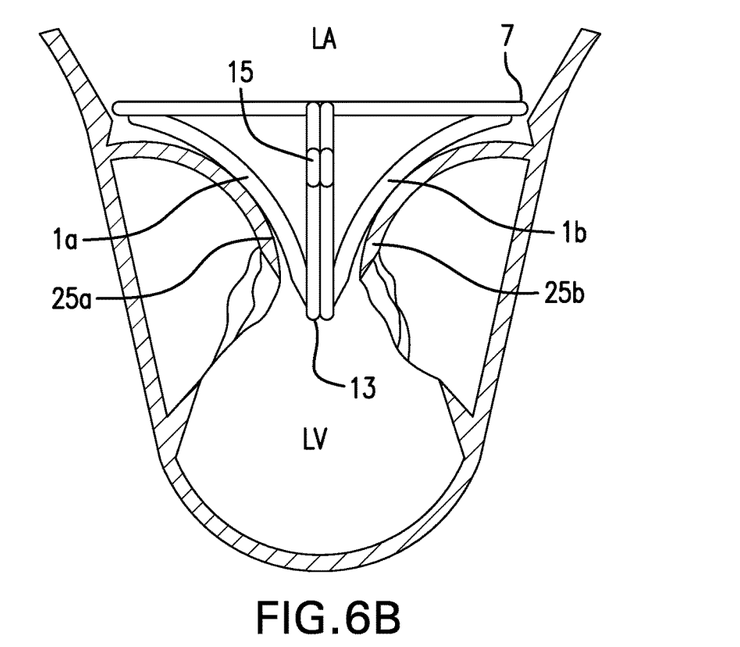
FIG. 6B is a front view of a patient's heart showing the deployment of the device of FIG. 1 at the mitral annulus position, with the valve in a closed position.
Figure 6C:
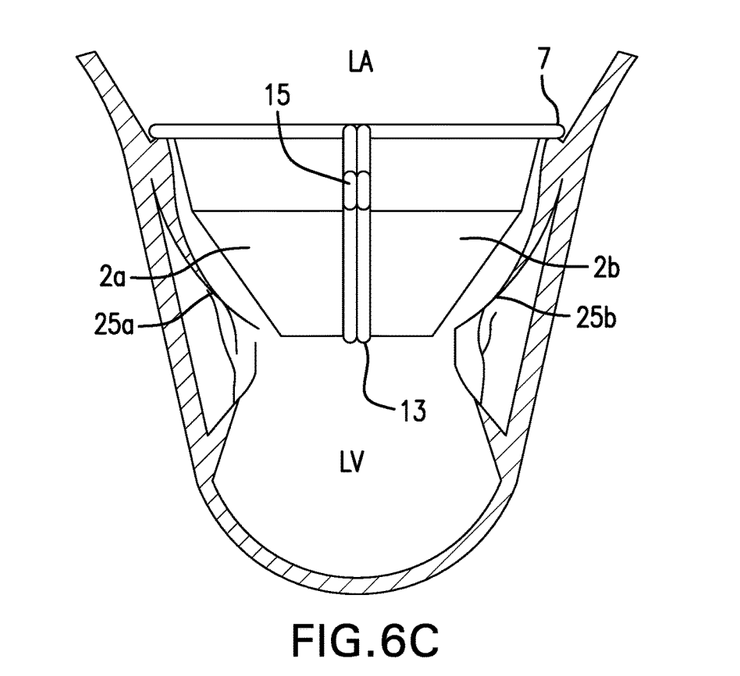
FIG. 6C is a front view of a patient's heart showing the deployment of the device of FIG. 1 at the mitral annulus position, with the valve in an opened position.
Figure 6D:
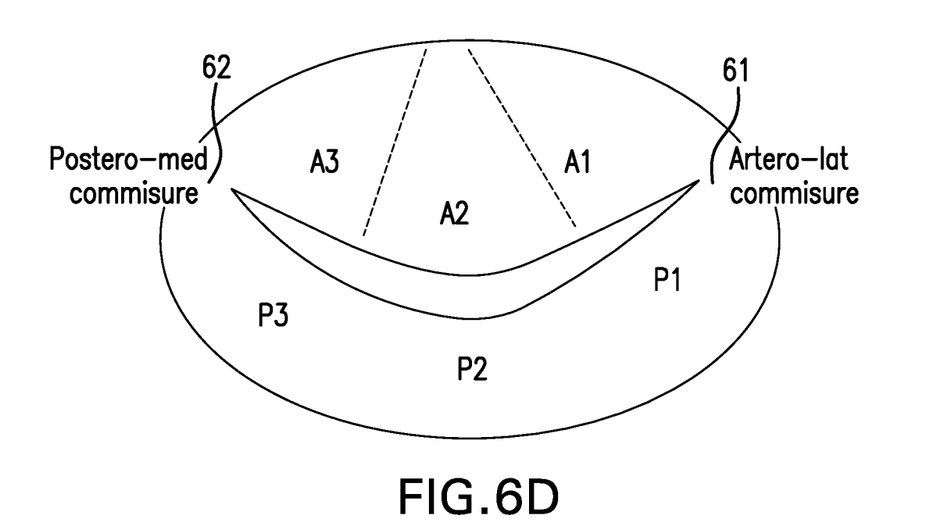
FIG. 6D is a top schematic view of a natural human mitral valve.

FIGS. 6A-6C illustrate the device 100 when it has been deployed at the mitral annulus position in a patient's heart. As shown in FIG. 6A, the commissure sections 9 and 10 are seated on the native annulus 22, and each native leaflet 25 is positioned between a gap G1 or G2 which is defined between the tail 131 and the leg 17, and the tail 141 and 18, respectively. In addition, the bends 13 and 14 of the wire frame 102 are inserted between the chordae and the native leaflets 25 to balance the device 100. This manner of securement allows the device 100 to be securely positioned at the location of the native annulus 22. In particular, the rounded ends 15 and 16 are positioned under the posteromedian commissure (PMC) and artero-lateral commissure (ALC), and the commissure sections 10 and 9 are positioned on the PMC and ALC at the locations 62 and 61, respectively, as shown in FIG. 6D. This positioning of the device 100 creates a strong anchoring clip effect which prevents the device 100 from moving up and down.

FIG. 6B shows the leaflet assembly 104 in a closed position, and FIG. 6C shows the leaflet assembly 104 in an opened position, where LA is the left atrium, and LV is the left ventricle. 25a is the native anterior leaflet, and 25b is the native posterior leaflet. FIG. 1C shows the valve opened, while FIGS. 1D and 1E show the valve closed.

The device 100 of the present invention can be compacted into a low profile and loaded onto a delivery system, and then delivered to the target location by a non-invasive medical procedure, such as through the use of a delivery catheter through transapical, or transfemoral, or transseptal procedures. The mitral valve replacement device can be released from the delivery system once it reaches the target implant site, and can expand to its normal (expanded) profile either by inflation of a balloon (for a balloon expandable supporting structure) or by elastic energy stored in the device (for a device with a self-expandable supporting structure).

Figure 7:
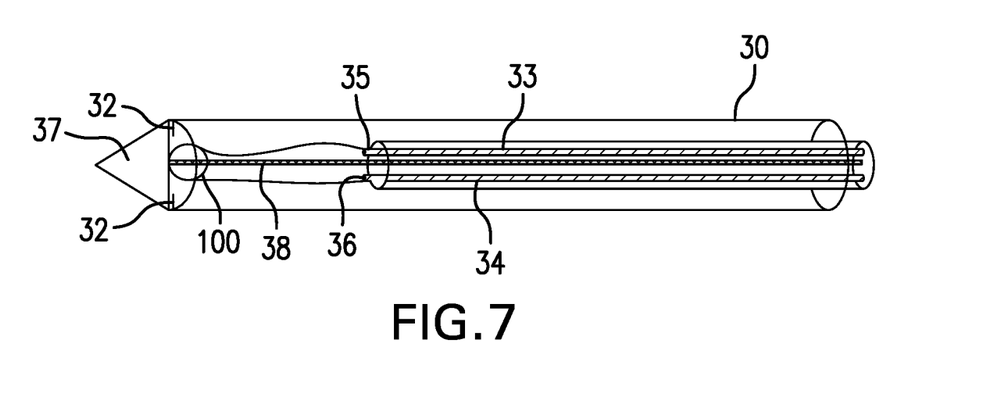
FIG. 7 illustrates a delivery system that can be used to deploy the device of FIG. 1.
Figure 7A:
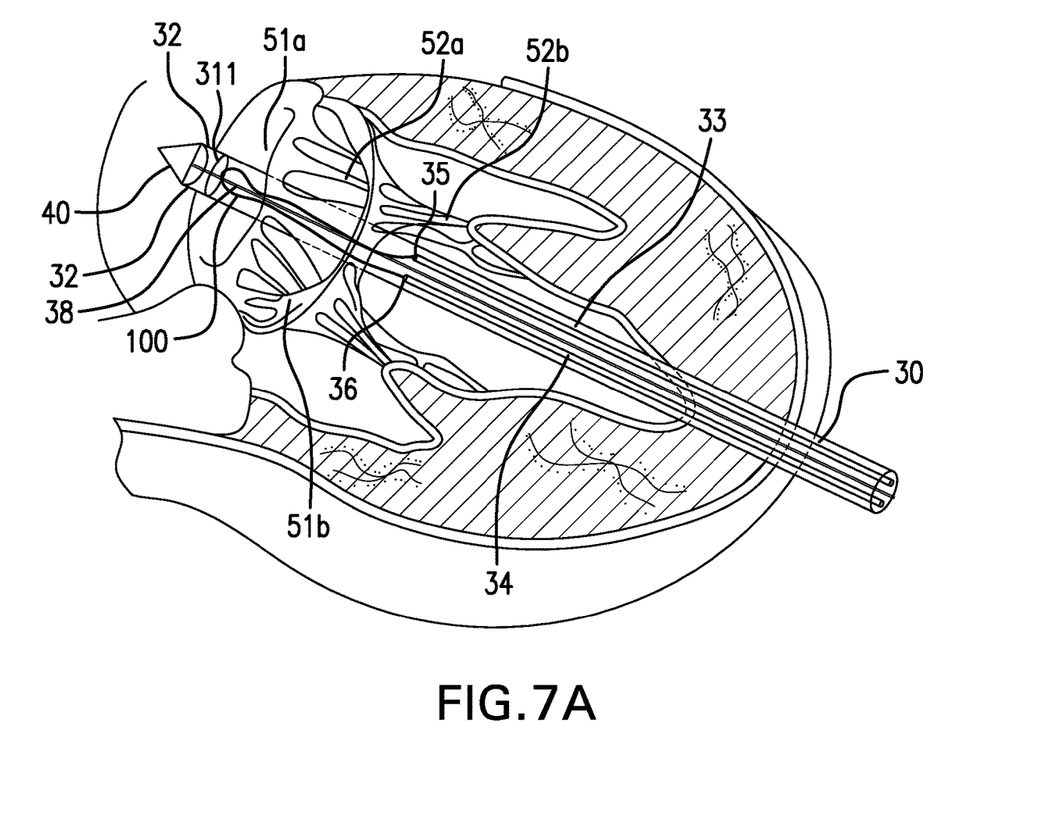
FIGS. 7A-7D illustrate how the device of FIG. 1 can be deployed at the mitral annulus of a patient's heart using a Transapical delivery system.
Figure 7B:
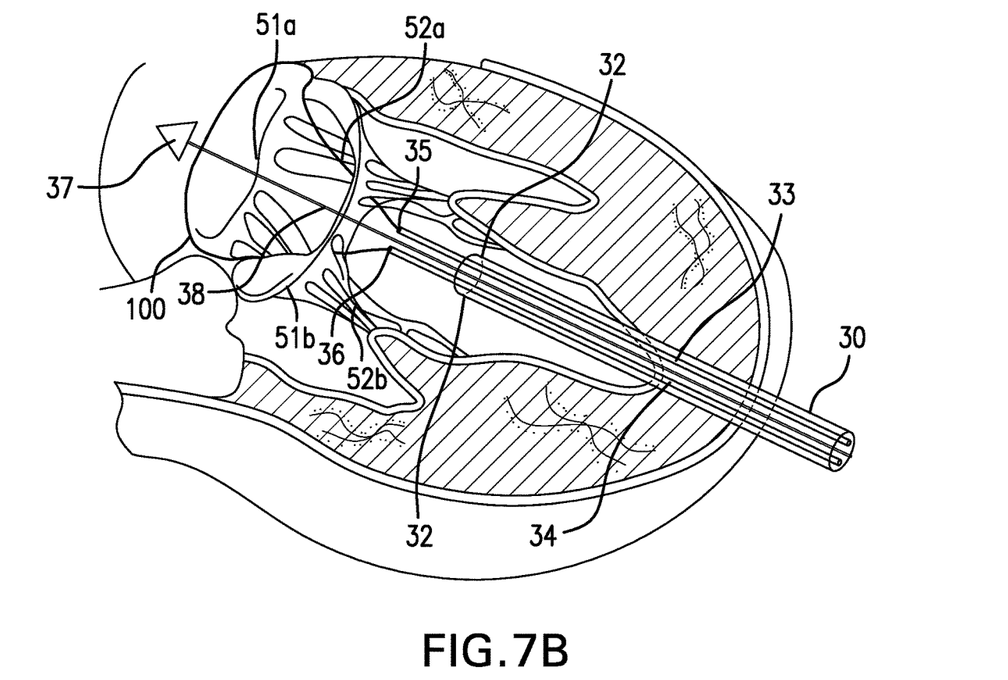
Figure 7C:
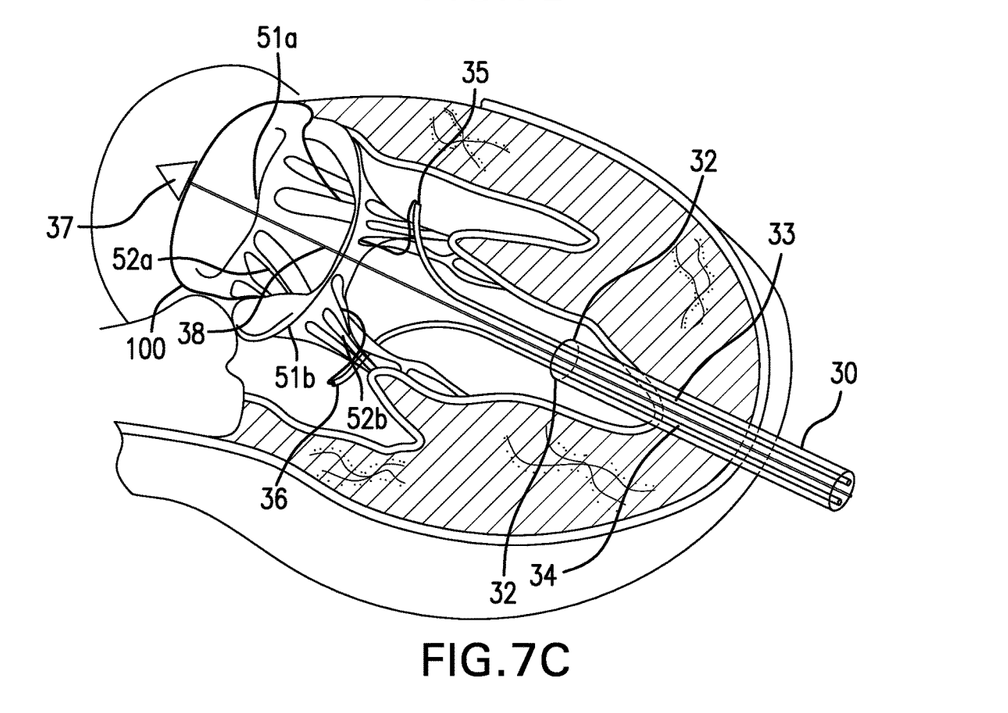
Figure 7D:
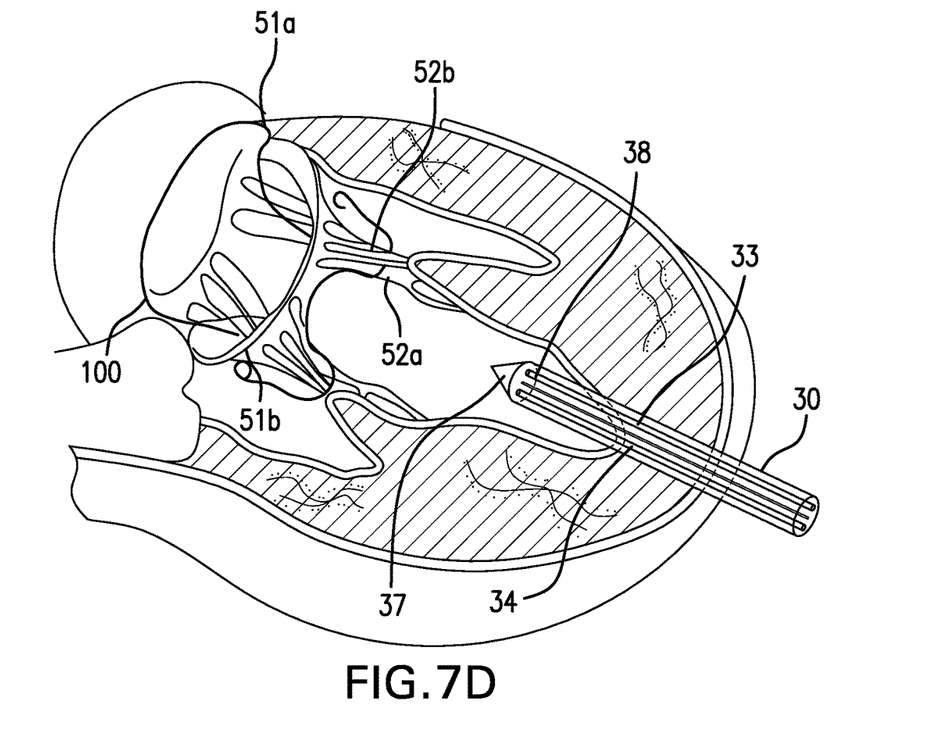

FIGS. 7 and 7A-7E illustrate how the device 100 can be deployed at the mitral annulus of a patient's heart using a transapical delivery system. Referring first to FIG. 7, the delivery system has a catheter which has an outer sheath 30 with a distal tip 37. A center tube 38 extends through the outer sheath 30 and is connected to the distal tip 37, and a marker band 311 (see FIG. 7A) is positioned at the distal end of the outer sheath 30. 32 indicates the left and right of the marker band 311. Two cables 35 and 36 extend through respective tubes 33 and 34, respectively, that run through the interior of the sheath 30. FIG. 7A illustrates the device 100 in a collapsed configuration being delivered to the mitral annulus inside the sheath 30. In FIG. 7B, the sheath 30 is withdrawn (i.e., moved downwardly) to expose the device so that the self-expanding wire frame 102 will deploy the anterior atrium annulus section 7 and the posterior atrium annulus section 8 in the atrium. In FIG. 7C, the sheath 30 is further withdrawn to release the two cables 35 and 36, and the cables 35 and 36 are detached so that the tails 131 and 141 of the wire frame 102 can be inserted in the chordae under the native commissure leaflet. As shown in FIGS. 7A-7D, 51a is the anterior leaflet, 51b is the posterior leaflet, 52a is the anterior chordae and 52b is the posterior chordae. Once this occurs, the device 100 is deployed at the native annulus, and in FIG. 7d, the delivery system can be withdrawn.

Thus, when the device 100 is deployed, the annulus sections 7 and 8 "seat" at the mitral annulus area to create a "seal" to prevent leakage (blood flow back from the left ventricle to the left atrium) from the area surrounding the device 100. This is best illustrated in FIGS. 6A-6C. In addition, the opening and closing motion of the valve design of the present invention is very similar to the opening and closing motion of a natural mitral valve.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A heart valve assembly, comprising:
    a leaflet support structure that comprises a wire frame having an anterior atrium annulus section and a posterior atrium annulus section, with each opposite end of the atrium annulus sections transitioning to a commissure section that curves radially inwardly along the same plane as the atrium annulus sections, and which then transitions via a first bend to a leg which extends vertically at opposite central points of the wire frame, each leg extending vertically and slightly radially outwardly at an angle, and each leg transitioning via a second bend which extends radially outwardly and transitions into a tail that extends vertically upwardly and generally parallel with the corresponding leg, with a gap defined between each corresponding tail and leg; and
    a leaflet assembly having exactly two leaflets that are stitched to the legs and the atrium annulus sections of the wire frame.

2. The assembly of claim 1, wherein each atrium annulus section extends horizontally and is shaped like half an oval.

3. The assembly of claim 1, wherein an extension is provided at about the central portion of each atrium annulus section and extends radially outwardly along the same plane as each atrium annulus section.

4. The assembly of claim 1, the wire frame defines shape selected from the group consisting of: an oval shape, a circular shape, and a D shape.

5. The assembly of claim 1, wherein each tail terminates at a rounded end which curves radially outwardly.

6. A heart valve assembly, comprising:
    a leaflet support structure that comprises a wire frame having an anterior atrium annulus section and a posterior atrium annulus section, with each opposite end of the atrium annulus sections transitioning to a commissure section that curves radially inwardly along the same plane as the atrium annulus sections, and which then transitions via a first bend to a leg which extends vertically at opposite central points of the wire frame, each leg extending vertically and slightly radially outwardly at an angle, and each leg transitioning via a second bend which extends radially outwardly and transitions into a tail that extends vertically upwardly and generally parallel with the corresponding leg, with a gap defined between each corresponding tail and leg, and wherein each tail terminates at a rounded end which curves radially outwardly;
    wherein an extension is provided at about the central portion of each atrium annulus section and extends radially outwardly along the same plane as each atrium annulus section; and
    a leaflet assembly having exactly two leaflets that are stitched to the legs and the atrium annulus sections of the wire frame.

\* \* \* \* \*